United States Patent
Jarl et al.

(10) Patent No.: US 8,249,722 B2
(45) Date of Patent: Aug. 21, 2012

(54) ACTIVE FIXATION ELEMENT

(75) Inventors: Per Jarl, Järfälla (SE); Rolf Hill, Järfälla (SE); Olof Stegfeldt, Sävsångarvägen (SE)

(73) Assignee: St. Jude Medical AB, Jarfalla (SE)

( * ) Notice: Subject to any disclaimer, the term of this patent is extended or adjusted under 35 U.S.C. 154(b) by 96 days.

(21) Appl. No.: 12/744,498

(22) PCT Filed: Nov. 29, 2007

(86) PCT No.: PCT/SE2007/050925
§ 371 (c)(1),
(2), (4) Date: May 25, 2010

(87) PCT Pub. No.: WO2009/070074
PCT Pub. Date: Jun. 4, 2009

(65) Prior Publication Data
US 2010/0234931 A1    Sep. 16, 2010

(51) Int. Cl.
*A61N 1/00* (2006.01)

(52) U.S. Cl. ...................................... 607/127

(58) Field of Classification Search ............. 607/127
See application file for complete search history.

(56) References Cited

U.S. PATENT DOCUMENTS

| | | | |
|---|---|---|---|
| 3,577,980 A * | 5/1971 | Cohen | 600/578 |
| 5,002,067 A | 3/1991 | Berthelsen et al. | |
| 5,354,327 A | 10/1994 | Smits | |
| 5,545,201 A | 8/1996 | Helland et al. | |
| 6,078,840 A | 6/2000 | Stokes | |
| 6,685,664 B2 * | 2/2004 | Levin et al. | 604/5.04 |
| 7,062,310 B2 | 6/2006 | Bernhart et al. | |
| 7,106,574 B2 * | 9/2006 | Beyerlein | 361/313 |
| 8,000,807 B2 * | 8/2011 | Morris et al. | 607/119 |
| 2002/0049439 A1 | 4/2002 | Mulier et al. | |

* cited by examiner

*Primary Examiner* — George Manuel

(57) ABSTRACT

A helical fixation element of an implantable medical lead. The fixation element has at least one blood drainage channel running along at least a tissue-penetrating portion of the helix windings of the fixation element. The channel guides, during penetration and anchoring of the fixation element and the lead in a tissue, blood leaking from the tissue away from the vicinity of the fixation element, thereby reducing the size of a fibrin clot formed around the fixation element. The capture threshold for stimulating the tissue is therefore reduced.

8 Claims, 7 Drawing Sheets

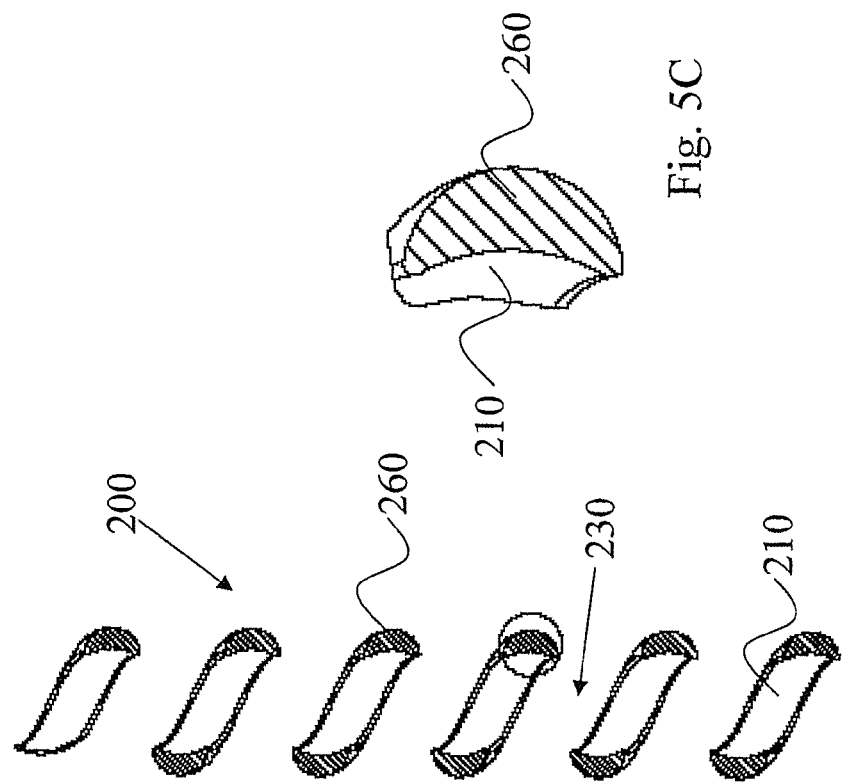
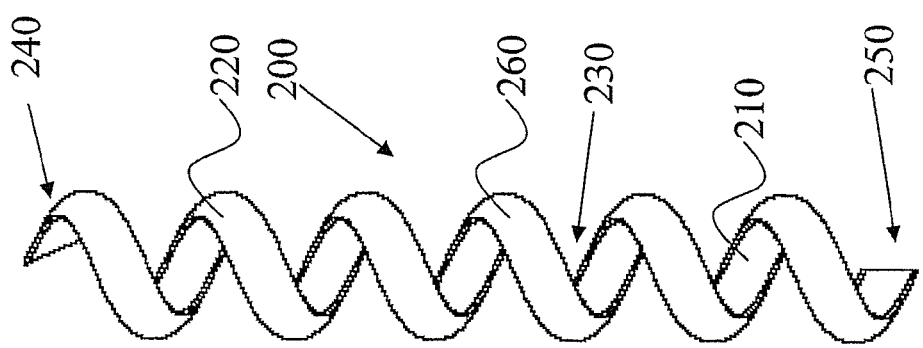

ACTIVE FIXATION ELEMENT

BACKGROUND OF THE INVENTION

1. Field of the Invention

The present invention generally relates to active fixation elements, and in particular such fixation elements for usage in implantable medical leads.

2. Description of the Prior Art

Body implantable electrical leads form the electrical connection between an implantable medical device (IMD), such as cardiac pacemaker or cardiac defibrillator, and body tissue, such as the heart, which is to be electrically stimulated. As is well known, the leads connecting the IMD with the tissue may be used for pacing/defibrillation and for sensing electrical signals produced by the tissue.

The implantable leads of today and in particular cardiogenic implantable leads can generally be divided into two classes depending on the tissue anchoring arrangement of the leads. Firstly, so-called passive fixation leads comprise radially protruding elements in the distal lead ends. These elements can become embedded in the trabecular network inside the heart and thereby provide an anchoring of the lead to the heart tissue. Examples of such protruding elements include collars, tines and fines. Passive leads are generally characterized by low chronic capture threshold and high impedance.

The other class of leads includes so-called active fixation leads. Such a lead typically comprises, in its distal end, a helical fixation element that can be screwed into the endocardium and myocardium to provide the necessary lead-to-tissue anchoring. Generally, active leads have superior ability to fixate without the need for any trabecular network.

When a helical fixation element penetrates the myocardium, it causes a local injury and bleeding typically occurs together with an inflammatory response. Blood will leak into the space between the endocardium and the myocardium, forming a blood pocket. Taken together these effects result in the formation of a blood clot and a fibrin network around the anchored fixation element. If the fixation element is also employed as one of the pacing and/or sensing electrodes of the lead, the formed blood clot will lead to higher capture thresholds and lower sensibility of the helical electrode.

The traditional approach of mitigating these problems has been to include a steroid plug or some other steroid source at the distal lead end. The steroid reduces the inflammatory response following the tissue anchoring and thereby decreases the amount of non-stimulable tissue (fibrin) around the fixation element.

SUMMARY OF THE INVENTION

However, even by using steroids in connection with implantation the problem associated with anchoring active fixation elements in tissue is not solved, though somewhat lessened. It is therefore a need for an active fixation element that prevents or at least reduces the formation of a blood clot and non-stimulable tissue in the vicinity of the element in the anchored tissue.

The present invention overcomes these and other drawbacks of the prior art arrangements.

It is a general object of the present invention to provide an active tissue fixation element of an implantable device.

It is another object of the invention to provide an active fixation element having a design promoting blood drainage from the vicinity of the fixation element.

Briefly, the present invention involves an active fixation element for anchoring an implantable medical lead, catheter or other medical device to a tissue in an animal body. The fixation element is equipped with at least one blood drainage channel running along at least a first portion of the windings of the fixation element. This first portion extends from a tissue penetrating end of the fixation element and towards the opposite end attachable to the lead/catheter/device. The at least one channel preferably runs along the whole length of the windings but can end at a distance from the lead-connecting end as long as the channel extends beyond the fixation element portion that is anchored in a body tissue.

The blood drainage channel is preferably defined as a groove in a helically shaped wire forming the active fixation element. In such a case, the groove preferably faces an inner diameter space confined by the helix windings or, alternatively, faces one of the ends of the fixation element.

The helical fixation element can have different cross-sectional shapes of its helical wire, including circular, elliptical, quadratic, rectangular, triangular, crescent, in addition to more complex cross-sectional configurations.

The at least one blood drainage channel will guide and drain blood that is released due to a tissue injury in connection with penetrating and anchoring the fixation element and its connected medical device to the tissue. The blood drainage will reduce the size of any blood and fibrin clot formed from the injury in the vicinity of the fixation element. As the thickness of this non-stimulable clot is reduced, the acute and chronic capture threshold for stimulating the tissue is therefore significantly reduced.

The invention offers the following advantages:
Guides blood away from the penetration and anchoring site;
Reduces the size of any fibrin clot formed as a consequence of the tissue injury in connection with the tissue penetration and anchoring operation;
Lowers both acute and chronic capture thresholds;
Allows a faster ingrowth of the active fixation element in the tissue; and
Can be used in connection with helical wire geometries having improved current density, fixation and stability properties.

Other advantages offered by the present invention will be appreciated upon reading of the below description of the embodiments of the invention.

BRIEF DESCRIPTION OF THE DRAWINGS

FIG. 5A is an illustration of a helical active fixation element according to another embodiment of the present invention.

FIG. 5B is a cross-sectional view of the fixation element of FIG. 5A.

FIG. 5C is a cross-sectional view of the helical wire of the fixation element of FIGS. 5A and 5B.

DESCRIPTION OF THE PREFERRED EMBODIMENTS

Figure 1:
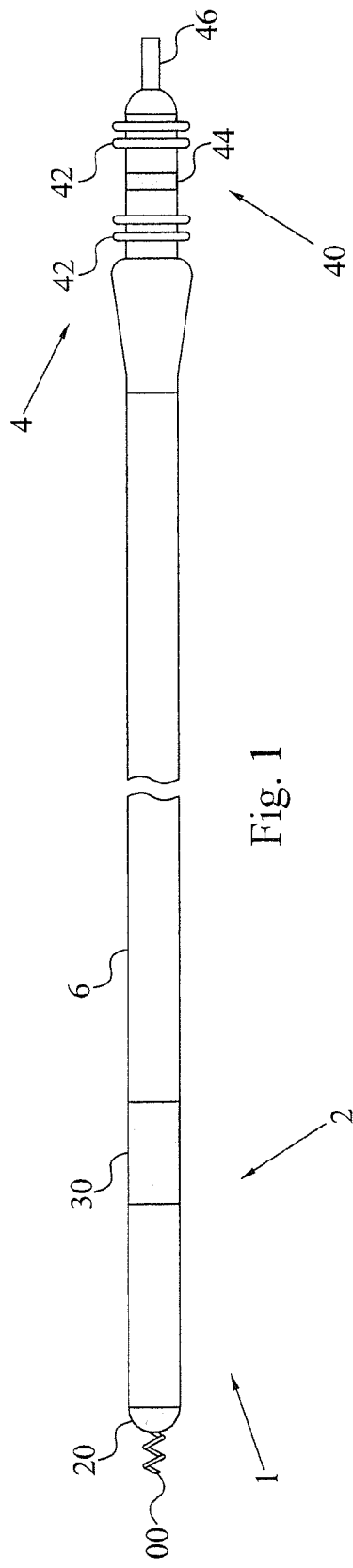
FIG. 1 is a side view of an implantable lead according to an embodiment of the present invention.

Throughout the drawings, the same reference characters will be used for corresponding or similar elements.

The present invention relates to implantable active fixation elements of implantable medical leads or catheters or other implantable devices, and in particular to such fixation elements having a helical configuration. The leads equipped with fixation elements of the invention are connectable to different implantable medical devices (IMDs), such as pacemakers, cardioverters, defibrillators and other implantable electrical medical devices.

The active fixation element of the present invention comprises at least one blood drainage channel running along at least a tissue-penetrating portion of the fixation element. This drainage channel will guide blood released during the penetration of the tissue, such as myocardium, out from the vicinity of the fixation element and, in the case of heart anchoring, out from the space between the myocardium and endocardium. Any resulting blood clot formed around the fixation element will therefore be much thinner and smaller as compared to the prior fixation elements. This will in turn have advantageous impact on the capture threshold in both the acute and chronic phase.

In the following, the present invention is described in more detail in connection with a helical fixation element to be used in an implantable medical lead. However, the helical fixation element of the invention is not limited to the usage of such leads but can be used in connection with other implantable devices having a need for anchoring the devices to a body tissue.

As is well known in the art, "proximal" relates, when applied to medical leads and their helical fixation elements, to the lead/helix portion facing the implantable medical device. Correspondingly, "distal" refers to the lead/helix portion facing the tissue, in which the lead/helix is (to be) anchored.

FIG. 1 is a schematic illustration of an implantable lead 1 equipped with a helical fixation element 100 according to an embodiment of the present invention. The lead 1 comprises a lead body 6 extending along a central, longitudinal axis. The lead 1 has a proximal end 4 carrying a connector assembly 40 for electrically connecting the lead body 6 to an IMD. The lead 1 also has a distal end 2 comprising a header with electrodes 20, 30 and the fixation element 100. The fixation element 100 is in the form of a helical, screw-in fixation element 100 adapted to be extended so as to project from the distal end of the header. The helical screw-in fixation element 100 is preferably active electrically so as to function as an electrode when implanted to stimulate selected tissue, such as cardiac tissue, and/or sense electrical activity of the tissue. Consistent with teachings well known in the art, one or more portions of such a helical electrode 100 may be electrically insulated along its length. The helical electrode 100 not only has a stimulating and/or sensing function but also serves to anchor or stabilize the distal lead portion 2 relative to the tissue.

The helical electrode 100 embodies a blood drainage channel according to the invention for guiding blood released in connection with tissue penetration out from the vicinity of the helical electrode 100 when anchored in tissue.

The distal lead portion 2 also has a tip electrode 20 and ring electrode 30 or indifferent electrode, well known in the art. These electrodes 20, 30 are provided for electrically stimulating adjacent tissue and/or for sensing electrical activity of tissue.

The connector assembly 40 at the proximal lead end 4 is adapted to electrically and mechanically couple the lead body 6 to the IMD. The assembly 40 comprises terminal contacts in the form of a tubular, rotatable pin terminal contact 46, often denoted connector pin, and a ring terminal contact 44, generally referred to as connector ring 44. These two contacts 44, 46 are positioned to engage corresponding electrical terminals within a receptacle in the IMD. In order to prevent ingress of body fluid into the IMD receptacle, the connector assembly 40 may be provided with spaced-apart sets of seals 42, well known in the art.

The present invention is not limited to electrically conducting helical screw-in fixation elements. In clear contrast, the teachings of the invention can be applied to helical screw-in fixation elements that are not employed as stimulating/sensing electrodes, i.e. being made of non-conducting material and/or having no electrical contact with electrical terminals in the IMD.

Figure 2:
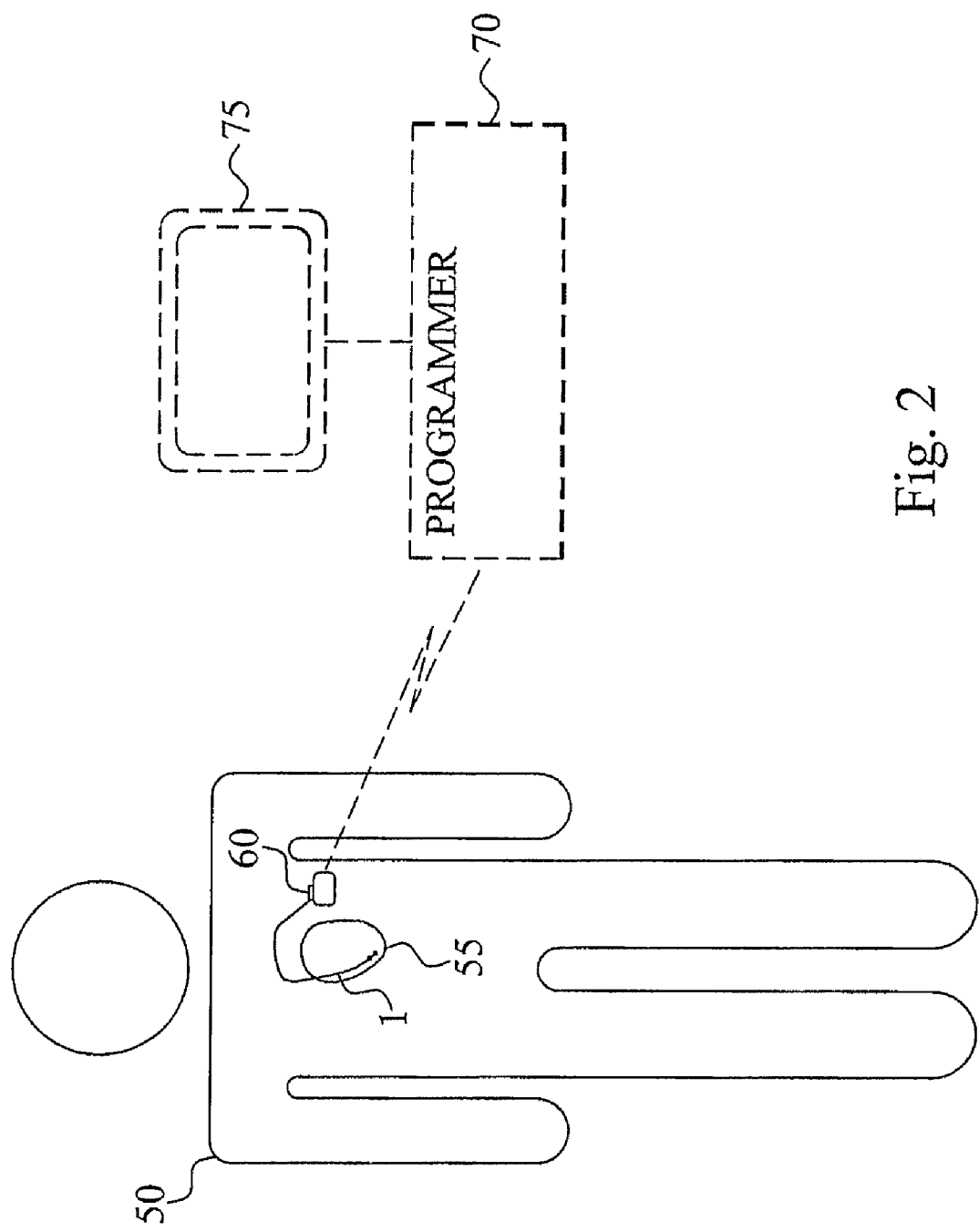
FIG. 2 is a schematic overview of a subject having an implantable medical device connected to an implantable lead according to an embodiment of the present invention.

FIG. 2 is a schematic overview of a subject 50 equipped with an IMD 60 connected to the subject's heart 55. The IMD 60 is illustrated as a device that monitors and/or provides therapy to the heart 55 of the patient 50, such as a pacemaker, defibrillator or cardioverter. However, the present invention is not limited to cardiac-associated IMDs but may also be practiced with other implantable medical devices, such as drug pumps, neurological stimulators, physical signal recorders, oxygen sensors, or the like, as long as the IMD 60 is equipped with or is connected to at least one medical lead 1 equipped with a helical fixation element according to the present invention.

The IMD 60 can wirelessly communicate with an external device 70, non-limitedly illustrated as a programmer 70 in the figure. The external device 70 could alternatively be a physician's workstation, a home monitoring device, a base station or actually any data processing unit having capability of receiving data collected by the IMD 60 and preferably sending instructions and commands to the IMD 60. The external device 70 is preferably connected to a display screen 75 allowing display of the collected diagnostic parameters and data It is anticipated by the present invention that a lead or catheter of the present invention does not necessarily have to be used in a human subject but can instead be implantable in other animal subjects, in particular mammalian subjects.

Figure 3:
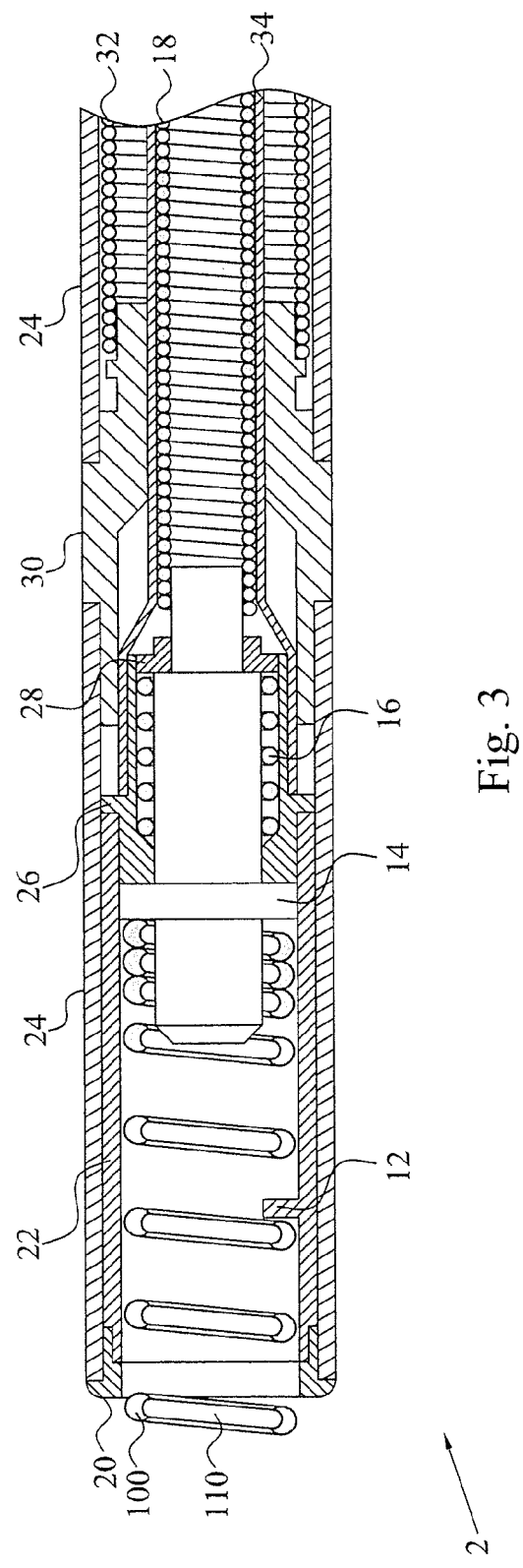
FIG. 3 is an axial cross section view of the distal portion of an implantable medical lead according to an embodiment of the present invention.

FIG. 3 is a cross-sectional view of the distal end 2 of the implantable lead of FIG. 1. The helix electrode 100 is mechanically and electrically connected to an inner coil conductor 18 by means of a helix shaft 14 manufactured by an electrically conductive material such as platinum, gold, tantalum, titanium or an alloy such as platinum/iridium, e.g. Pt/Ir 90/10 or 80/20. The helix shaft 14 or at least a portion thereof is preferably made of a high density, electrically conductive material to be radiopaque. The lead-connecting (proximal) end of the helix electrode 100 and the distal end of the inner coil conductor 18 may be attached by, for instance laser welding or the like, to the opposite ends of the helix shaft 14. The shaft 14 is journaled for rotation and axial movement within a sleeve 26 and includes a radially extending flange defining a proximal, radially-extending surface engageable against a distal extremity of the sleeve to limit the retraction of the helix electrode 100. The sleeve 26 is preferably electrically conductive and secured to an inner conductive tube 22 ending at the tip electrode 20. The sleeve 26 and the conductive tube 22 are preferably made of an electrically conducting low density metal, such as titanium, or metal alloy, such as MP35N® or stainless steel.

The proximal portion of the sleeve 26 has a counterbore terminating at a distal end wall. An electrically conductive tubular abutment 28, such as of MP35N® or the like, L-shaped in cross section, has an axial portion connected, e.g. welded, to the proximal end of the helix shaft 14 and a flange projecting radially within the counterbore of the sleeve 26. Thus, the abutment 28 being secured to the shaft 14 is movable rotationally and axially with the shaft 14 relative to the sleeve 26.

Contained within the counterbore is an electrically conductive, expandable/contractible contact member, preferably in the form of a metallic compression spring 16 of, for instance, MP35N® or like material. In such a case, electrically continuity is thereby established between the tip electrode 20 and the terminal contact pin of the connector assembly via the inner tube 22, the sleeve 26, the contact spring 16, the L-shaped abutment 28 and the inner conductor coil 18. The contact spring 16 is extended or contracted depending on the extension or retraction of the helix electrode 100.

An outer insulating tube 24, for instance of silicone rubber or polyurethane, extends between the proximal face of the tip electrode 20 and the distal extremity of the ring electrode 30. A corresponding insulating tube 24 also covers the main lead body by extending from the proximal extremity of the ring electrode 30 up to the connector assembly.

Projecting radially inwardly from the inner surface of the inner header tube 22 is a post 12 interposed between adjacent turns of the helix electrode 100. In this fashion, rotation of the helix electrode 100 forces the electrode 100 to advance or retract within the lead body header. As is seen in the figure, the helix 100 has a blood drainage channel 110 in the form of a groove extending from the tissue-penetrating end of the helix 100 to the helix end that is connected to the shaft 14 in the lead.

The ring electrode 30 is in mechanical and electrical contact with a terminal of the collector assembly, such as the collector ring, through an outer coil conductor 32. The two coil conductors 18, 32 are electrically insulated by a longitudinally extending insulating tube 34, such as made of silicone rubber, polyurethane or the like. This insulator 34 is disposed between the coils 18, 32 to prevent electrical contact between the conductors 18, 32 and between the ring electrode 30 and the inner conductor coil 18.

Even though not illustrated in the figure, the implantable medical lead can contain a steroid plug attached to the helix 100 of the present invention, or some other steroid source, well-known in the art. The steroid will leak out to the vicinity of the cardiogenic muscle and reduce the severity of an inflammatory reaction, thereby even further reducing the amount of non-stimulable connective tissue around the helix 100 when anchored in the myocardium.

Herein follows a more detailed description of particular embodiments of the active fixation element according to the present invention. These embodiments comprise one or more blood drainage channels running along at least a tissue-penetrating portion of the helical windings of the fixation element. The tissue-penetrating portion is the portion of the fixation element to be anchored in a tissue and therefore the portion opposite to the device-connecting portion that is attached to the lead.

The blood drainage channel does not necessarily have to run along the whole length of the fixation element. In clear contrast, in some application it is well enough that the distal helix portion that is anchored in the tissue comprises the blood drainage channel. The channel can then end shortly outside the anchored portion. For the purpose of endocardial anchoring, the drainage channel preferably runs at least along the portion of the fixation element that is anchored in the myocardium and the portion which is in the space between the myocardium and the endocardium to allow blood leaked from the myocardium to be drained therefrom and out through the endocardium into a heart chamber.

However, the at least one blood drainage channel preferably runs along the whole length of the helical fixation element or at least along the length of the helical fixation element that protrudes out from the uttermost distal end of the medical lead. This means that any helical windings still present in the lead header following tissue anchoring does not necessarily have to be equipped with the drainage channel of the invention.

Figure 4C:
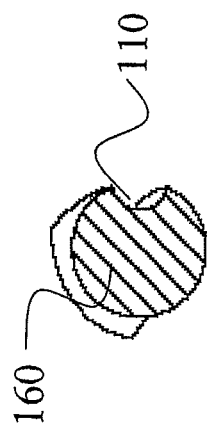
FIG. 4C is a cross-sectional view of the helical wire of the fixation element of FIGS. 4A and 4B.
Figure 4B:
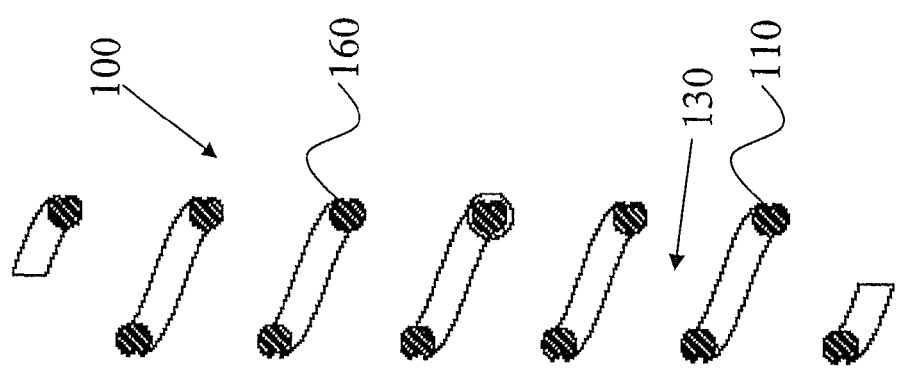
FIG. 4B is a cross-sectional view of the fixation element of FIG. 4A.
Figure 4A:
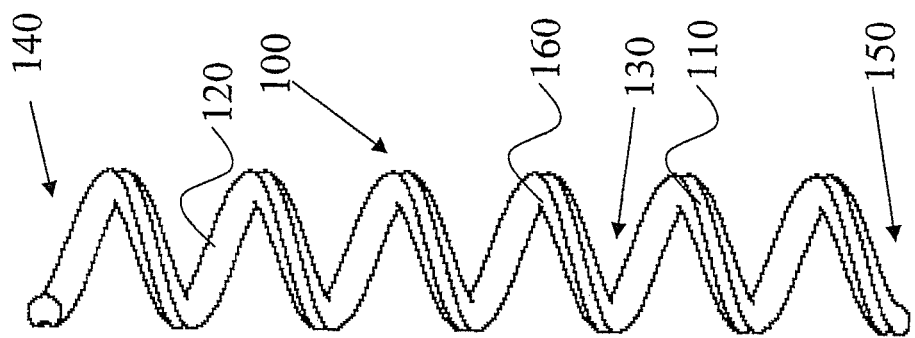
FIG. 4A is an illustration of a helical active fixation element according to an embodiment of the present invention.

A first embodiment of the helical fixation element is illustrated in FIGS. 4A to 4C. FIG. 4A illustrates a three-dimensional view of the helical fixation element 100. FIG. 4B is a cross-sectional view of the fixation element 100 and FIG. 4C is a cross-sectional view of the helical wire 160 forming the fixation element 100. As is seen in the figures, the fixation element 100 has a general circular cross-section and can therefore be manufactured from a round wire 160. However, in clear contrast to the prior art fixation elements, a blood drainage channel 110 in the form of a groove or recesses 110 in the helical wire 160 runs along the helical windings 120 from the distal helix end 140 to the proximal lead end 150.

In the figures, the groove 110 is running along the windings 120 and faces radially out from an inner diameter space 130 confined by the helix windings 120. The present invention is though, no limited to such a relative channel positioning in the wire 160. In an alternative embodiment, the groove 110 is running along the windings 120 and faces towards the inner diameter space 130 confined by the helix windings, i.e. basically opposite to what is illustrated in FIG. 4B.

The cross-sectional configuration of the helix wire 160 is circular in FIGS. 4A-4C. The present invention is, though, not limited to circular cross-sectional configurations but can also use elliptical wire cross-sections. In such a case, the major axis of the ellipse can be in the longitudinal direction of the fixation element 100 or, alternatively, perpendicular to the longitudinal direction. One or more grooves can run in the elliptical wire 160, such as facing the inner diameter space 130, facing the tissue-penetrating (distal) helix end 140, facing the device-connecting (proximal) helix end 150 or facing radially out from inner space 130.

A second embodiment is illustrated in FIGS. 5A to 5C. The helix wire 260 has a crescent-shaped cross-section. In similarity to the first embodiment, the helical fixation element 200 has a drainage channel 200 but facing the inner diameter space 230 defined by the helical windings 220. The crescent-shape implies that the inwardly facing side of the wire 260 forms a channel 210 along which blood can flow out and away from the penetration site along the channel 210. The cross-sectional configuration has generally a shape produced when a circular disk has a segment of another circle removed from its edge, so that what remains is a shape enclosed by two circular arcs of different diameters which intersect at two points. The relative radiuses of the two circles define the shape of the blood drainage channel 210. If the other circle has a larger radius as compared to the circular disk, the channel 210 becomes shallower as compared to when the radius of the other circle is smaller than the radius of the circular disk. In such a case, the blood drainage channel 210 is defined by a concavely shaped surface of the wire 260. For blood drainage purposes, both ways work well.

The channel 210 preferably extends from the tissue-penetrating helix end 240 to the device-connecting end 250. In an alternative embodiment, the drainage channel 210 faces outwards, i.e. diametrically away from the confined inner space 230.

Compared to the helix embodiment disclosed by FIGS. 4A to 4C, the second embodiment has a better penetration design that is more suited for penetrating the endocardium and the myocardium while reducing the caused tissue injury. The helical fixation element also has improved ability to withstand pull forces on the distal lead end when the helix is fully extended in the tissue. Since the crescent-shape implies the formation of edges on the windings 220, the current density increases at the edges, thereby allowing a reduction in the energy consumption in connection with tissue stimulation.

Figure 6C:
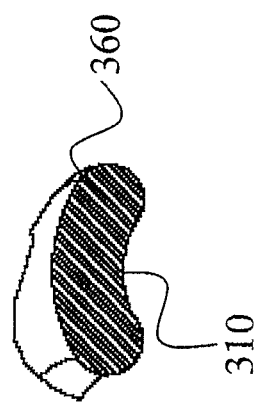
FIG. 6C is a cross-sectional view of the helical wire of the fixation element of FIGS. 6A and 6B.
Figure 6B:
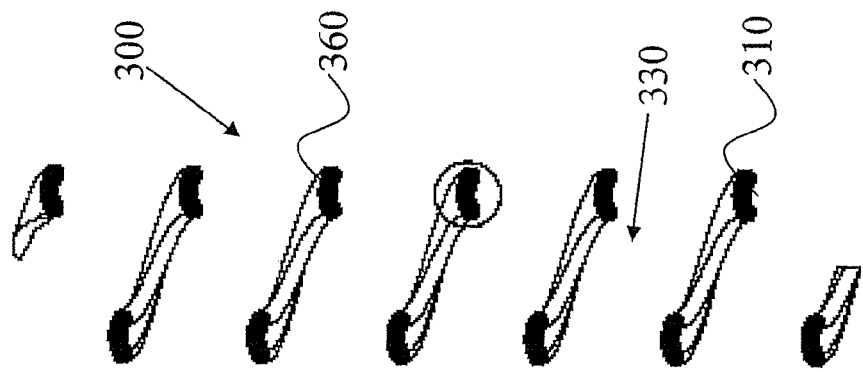
FIG. 6B is a cross-sectional view of the fixation element of FIG. 6A.
Figure 6A:
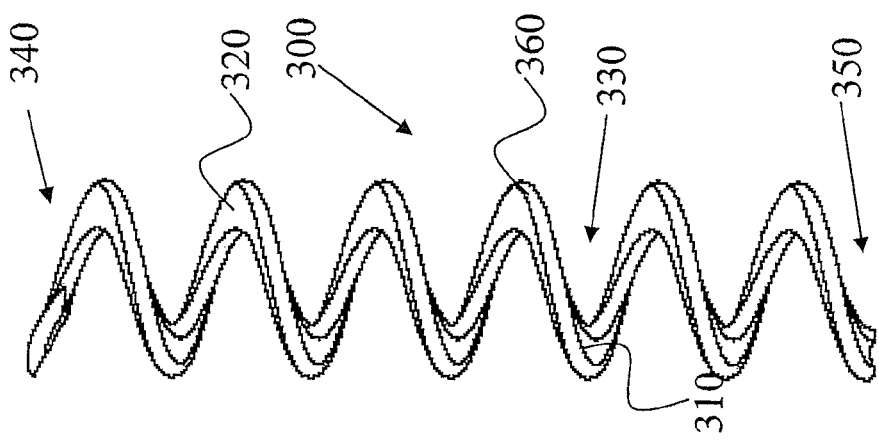
FIG. 6A is an illustration of a helical active fixation element according to a further embodiment of the present invention.

A third embodiment of a helical fixation element 300 according to the present invention is illustrated in FIGS. 6A to 6C. Compared to the previous embodiments, the cross-sectional dimension of the helix wire 360 is smaller in the direction of the longitudinal axis of the fixation element 300 than in a direction transverse to the longitudinal axis. The helical wire 360 can have a general rectangular cross-section with a drainage channel running along the helix windings 320 from the tissue-penetrating end 340 and preferably up to the device-connecting end 350. The channel 310 is preferably formed in at least one of the longer sides of the rectangular, implying that the channel 310 is facing the device-connecting 350 or the tissue-penetrating 340 end of the fixation element 300.

Instead of utilizing a rectangular cross-section, the wire 360 can be elliptical with the major axis perpendicular to the longitudinal helix axis. FIGS. 6A to 6C illustrate such an embodiment with the drainage channel 310 in the form of a shallow groove 310 in the wire body 360. As is better seen in FIG. 6, the side of the helical wire 360 facing the tissue-penetrating end 340 is convex, while the opposite side facing the device-connecting end 250 is concave and houses the blood channel 310. In an alternative embodiment, the concave, channel-housing side is instead facing the tissue-penetrating end 340 leaving the convex side facing the opposite helix end 35.

The helix wire 360 can instead be equipped with two drainage channels 310, preferably provided in connection with opposite sides of the rectangular/elliptical wire 360. In such a case, the wire 360 will have a waist, preferably a centrally positioned waist. This principle can of course be extended to the situation where drainage channels 310 are provided at more than two sides of a rectangular wire 360 and in connection with more than two end points of an elliptical wire 360.

This helix embodiment has improved tissue penetrating and fixation properties as compared to the previously disclosed embodiments. In the case of rectangular wire cross-section, the current density will be very high. An elliptic cross-section does typically not reach such high current densities but are still generally superior to circular cross sections. The bending properties and helix stiffness is improved in this helix embodiment.

Figure 7C:
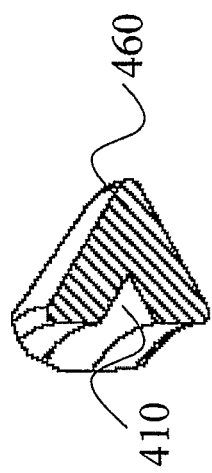
FIG. 7C is a cross-sectional view of the helical wire of the fixation element of FIGS. 7A and 7B.
Figure 7B:
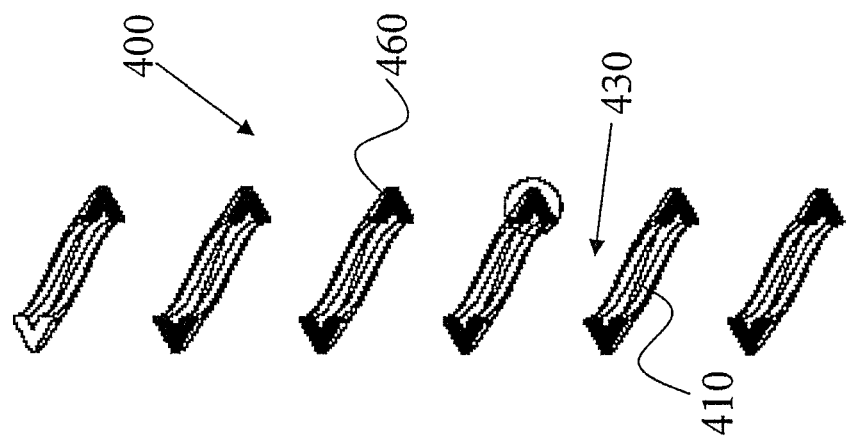
FIG. 7B is a cross-sectional view of the fixation element of FIG. 7A.
Figure 7A:
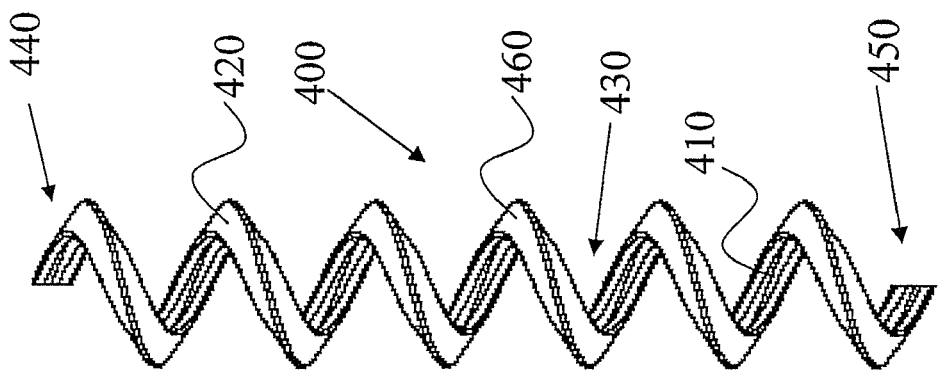
FIG. 7A is an illustration of a helical active fixation element according to yet another embodiment of the present invention.

FIGS. 7A to 7C illustrate yet another active fixation element embodiment of the present invention. The helical wire 460 forming the fixation element 400 has a triangular cross-section, preferably an equilateral triangle or an isosceles triangle. In either case, the base of the triangle (preferably the shortest side of an isosceles triangle) faces in the inner diameter space 430 confined by the helix windings 420. As a consequence, a corner of the triangle will face towards the outer surface of the fixation element 400.

A drainage channel 410 in the form of a small groove runs, preferably along the triangle base facing the inner diameter space 430. It is anticipated by the present invention that the drainage channel 410 could alternatively be situated in connection any of the other triangle sides, i.e. the side facing the device-connecting (proximal) 450 or tissue-penetrating (distal) 440 helix end. It is also possible to have a triangular helix wire 430 equipped with multiple, i.e. at least two, parallel drainage channels 410. In such a case, the drainage channels 410 can be provided in connection with respective triangle sides.

This fixation element embodiment has improved penetration ability as compared to traditional circular wire cross-sections. Furthermore, due to the triangular shape, the current density is significantly advantageous in this embodiment as compared to previously disclosed fixation elements.

Figure 8C:
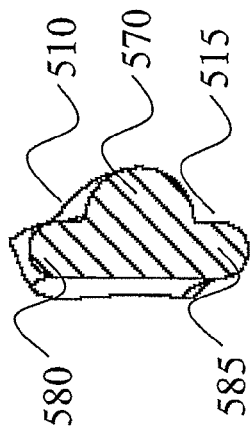
FIG. 8C is a cross-sectional view of the helical wire of the fixation element of FIGS. 8A and 8B.
Figure 8B:
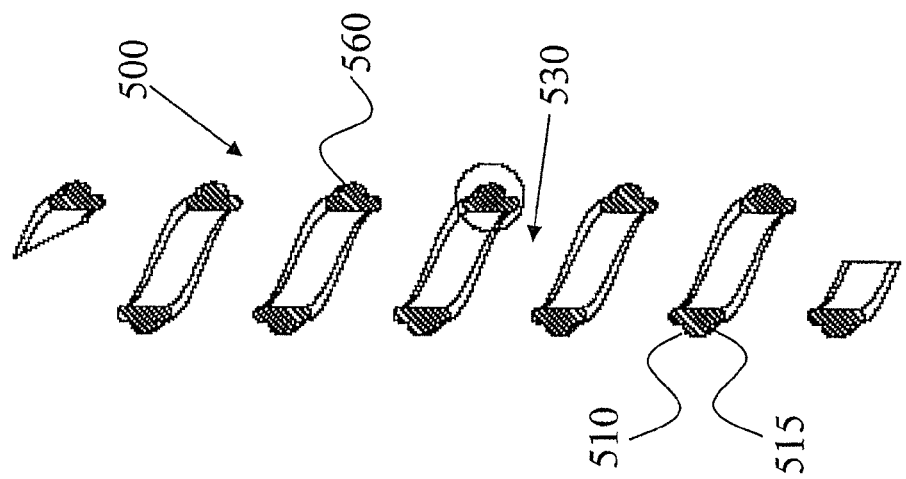
FIG. 8B is a cross-sectional view of the fixation element of FIG. 8A.
Figure 8A:
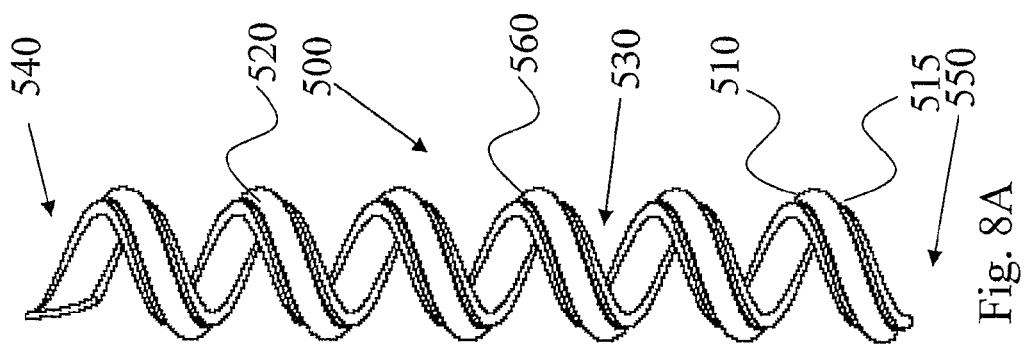
FIG. 8A is an illustration of a helical active fixation element according to a further embodiment of the present invention.

FIGS. 8A to 8C illustrate a further embodiment of a helical fixation element 500 according to the present invention. This fixation element 500 is formed of a helical wire 560 having a circular cross-section with extended side walls. Thus, the wire 560 can be regarded as consisting of a round central core 570 having protruding flanges 580, 585 running along the length of the wire 560. The opposite flanges 580, 585 are preferably parallel and situated on opposite sides of the central core 570. The flanges 580, 585 can extend out from an end of the circle 570 as illustrated in FIG. 8C. In such a case, the wire-cross section has the general shape of a floor formed by the two flanges 580, 585 with a central arc-shaped protrusion due to the central core 570. In such a case, two blood drainage channels 510, 515 are defined by the respective flanges 580, 585 and the central core 570. The drainage channels 510, 515 face away from the central inner diameter space 530 enclosed by the helix windings 520, one 510 towards the tissue-penetrating end 540 and the other 515 towards the device-connecting end 550.

If the two flanges instead would be radially protruding flanges 580, 585 positioned diametrically on opposite side of the central circular core 570, four drainage channels 510, 515 are formed. Two of the channels face inwards towards the inner diameter space 530, while the remaining two face in the outwards in the opposite direction.

This embodiment of the helical fixation element 500 has excellent current density properties and very good, penetration and fixation characteristics.

The cross-sectional wire profiles of the fixation element embodiments disclosed herein should be seen as illustrative but preferred wire profiles. The basic concept of the invention, i.e. equipping a helical active tissue fixation element with at least one drainage channel can be applied to any wire or fixation element geometry. The present invention therefore also encompasses such non-disclosed but obvious wire profiles as long as they comprise at least one longitudinally extending blood drainage channel.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical lead comprising:
    a longitudinally extending body including a proximal end and a distal end;
    a connector assembly at the proximal end of the longitudinally extending body, the connector assembly configured to electrically connect with an implantable medical device;
    a header at the distal end of the longitudinally extending body;
    a fixation element extending distally from the header, the fixation element adapted to secure the lead to blood-containing tissue, the fixation element having a helical structure comprising a tissue-penetrating portion configured to penetrate the blood-containing tissue; and
    a blood drainage channel in the helical structure proceeding along at least the tissue-penetrating portion thereof, and configured to drain blood from the tissue.

2. The implantable medical lead as claimed in claim 1 wherein the helical structure has a length and wherein the blood drainage channel proceeds along an entirety of the length.

3. The implantable medical lead as claimed in claim 1 wherein the blood drainage channel is formed by a groove in the helical structure proceeding along at least the tissue-penetrating portion.

4. The implantable medical lead as claimed in claim 3 wherein the helical structure comprises helix windings defining an interior space within the helix windings, and wherein the groove faces the interior space.

5. The implantable medical lead as claimed in claim 3 wherein the tissue-penetrating portion comprises a tissue-penetrating tip, and wherein the helical structure comprises an opposite end opposite the tip, and wherein the groove faces at least one of the tip and the opposite end.

6. The implantable medical lead as claimed in claim 1 wherein the helical structure is a helically wound wire.

7. The implantable medical lead as claimed in claim 6 wherein the wire has a crescent-shaped cross-section that forms the blood-drainage channel.

8. An implantable medical lead comprising:
    a housing configured for implantation in vivo in a subject, the housing comprising medical-therapy generating components;
    a helical fixation element mechanically connected to at least one of said the medical therapy generating components and configured to deliver medical therapy generated by the medical therapy generating components to tissue in vivo; and
    the helical fixation element comprising a helical structure having a tissue-penetrating portion configured to penetrate blood-containing tissue, and a blood drainage channel formed in the helical structure and configured to drain blood from the tissue.

* * * * *